United States Patent
Sode

(10) Patent No.: US 7,067,295 B1
(45) Date of Patent: Jun. 27, 2006

(54) GLUCOSE DEHYDROGENASE

(76) Inventor: Koji Sode, 1-13-16, Minami, Meguro-Ku, Tokyo 152-0013 (JP)

( * ) Notice: Subject to any disclaimer, the term of this patent is extended or adjusted under 35 U.S.C. 154(b) by 0 days.

(21) Appl. No.: 09/958,231

(22) PCT Filed: Apr. 10, 2000

(86) PCT No.: PCT/JP00/02322

§ 371 (c)(1),
(2), (4) Date: Oct. 5, 2001

(87) PCT Pub. No.: WO00/61730

PCT Pub. Date: Oct. 19, 2000

(30) Foreign Application Priority Data

Apr. 8, 1999 (JP) .................................. 11-101143
Jan. 18, 2000 (JP) ............................ 2000-009152

(51) Int. Cl.
*C12N 9/04* (2006.01)
*C12N 15/00* (2006.01)
*C07H 21/04* (2006.01)
*C12Q 1/32* (2006.01)
*C12P 21/04* (2006.01)
*C12N 1/20* (2006.01)
*C12Q 1/00* (2006.01)
*C12Q 1/68* (2006.01)

(52) U.S. Cl. ........................... 435/190; 435/440; 435/4; 435/6; 435/26; 435/69.1; 435/71.1; 435/252.3; 435/320.1; 536/23.2; 536/23.7

(58) Field of Classification Search ................ 435/190, 435/440, 4, 6, 252.3, 320.1, 69.1, 71.1, 26; 536/23.2, 23.7
See application file for complete search history.

(56) References Cited

FOREIGN PATENT DOCUMENTS

EP           A 78636        5/1983
JP           A11-243949     9/1999

OTHER PUBLICATIONS

Witarto et al., Applied Biochemistry and Biotechnology, vol. 77-79, pp. 159-168 (1999).
Murzin A.G., Proteins: Structure, and Genetics, vol. 14, No. 2, pp. 191-201 (1992).
Anthony C. et al., Progress in Biophysics and Molecular Biology, vol. 69, No. 1, pp. 1-21, (1998).

(Continued)

*Primary Examiner*—Ponnathapura Achutamurthy
*Assistant Examiner*—Yong D. Pak
(74) *Attorney, Agent, or Firm*—Birch, Stewart, Kolasch & Birch, LLP

(57) ABSTRACT

Modified water-soluble glucose dehydrogenase having pyrrolo-quinoline quinone as a coenzyme are provided wherein at least one amino acid residue is replaced by another amino acid residue in a specific region. Modified water-soluble PQQGDHs of the present invention have improved thermal stability.

6 Claims, 7 Drawing Sheets

OTHER PUBLICATIONS

Sode K. et al., Enzyme and Microbial Technology, vol. 26, No. 7, pp. 491-496 (2000).

Igarashi et al., Biochem. Biophys. Res. Commun., vol. 264, No. 3, pp. 820-824 (1999).

Cleton-Jansen et al., Mol. Gen. Genet., vol. 217, No. 2-3, pp. 430-436 (1989).

Yoshida et al., ProteinEng., vol. 12, No. 1, pp. 63-70 (1999).

Sode et al., J. Biotechnol., vol. 49, No. 103, pp. 239-243 (1996).

FIG. 4

| | Wild-type | S231K | S231C | S231L | S231D | S231N | S231M | S231H |
|---|---|---|---|---|---|---|---|---|
| Glucose | 100 | 100 | 100 | 100 | 100 | 100 | 100 | 100 |
| 2-Deoxy-D-glucose | 4 | 5 | 3 | 2 | 6 | 5 | 5 | 2 |
| Mannose | 13 | 10 | 8 | 9 | 13 | 12 | 9 | 12 |
| Allose | 47 | 43 | 46 | 38 | 62 | 61 | 43 | 57 |
| 3-o-Methyl-D-glucose | 81 | 82 | 76 | 71 | 105 | 109 | 80 | 86 |
| Galactose | 11 | 15 | 14 | 12 | 20 | 18 | 10 | 17 |
| Xylose | 7 | 5 | 8 | 8 | 12 | 15 | 8 | 7 |
| Lactose | 61 | 59 | 69 | 54 | 73 | 66 | 56 | 56 |
| Maltose | 61 | 70 | 69 | 38 | 76 | 51 | 41 | 38 |

SEQUENCE LISTING

```
<160> NUMBER OF SEQ ID NOS: 16

<210> SEQ ID NO 1
<211> LENGTH: 454
<212> TYPE: PRT
<213> ORGANISM: Acinetobacter calcoaceticus

<400> SEQUENCE: 1

Asp Val Pro Leu Thr Pro Ser Gln Phe Ala Lys Ala Lys Ser Glu Asn
  1               5                  10                  15

Phe Asp Lys Lys Val Ile Leu Ser Asn Leu Asn Lys Pro His Ala Leu
                 20                  25                  30

Leu Trp Gly Pro Asp Asn Gln Ile Trp Leu Thr Glu Arg Ala Thr Gly
             35                  40                  45

Lys Ile Leu Arg Val Asn Pro Glu Ser Gly Ser Val Lys Thr Val Phe
         50                  55                  60

Gln Val Pro Glu Ile Val Asn Asp Ala Asp Gly Gln Asn Gly Leu Leu
 65                  70                  75                  80

Gly Phe Ala Phe His Pro Asp Phe Lys Asn Asn Pro Tyr Ile Tyr Ile
                 85                  90                  95

Ser Gly Thr Phe Lys Asn Pro Lys Ser Thr Asp Lys Glu Leu Pro Asn
                100                 105                 110

Gln Thr Ile Ile Arg Arg Tyr Thr Tyr Asn Lys Ser Thr Asp Thr Leu
            115                 120                 125
```

-continued

```
Glu Lys Pro Val Asp Leu Leu Ala Gly Leu Pro Ser Ser Lys Asp His
    130                 135                 140
Gln Ser Gly Arg Leu Val Ile Gly Pro Asp Gln Lys Ile Tyr Tyr Thr
145                 150                 155                 160
Ile Gly Asp Gln Gly Arg Asn Gln Leu Ala Tyr Leu Phe Leu Pro Asn
                165                 170                 175
Gln Ala Gln His Thr Pro Thr Gln Gln Glu Leu Asn Gly Lys Asp Tyr
            180                 185                 190
His Thr Tyr Met Gly Lys Val Leu Arg Leu Asn Leu Asp Gly Ser Ile
        195                 200                 205
Pro Lys Asp Asn Pro Ser Phe Asn Gly Val Val Ser His Ile Tyr Thr
    210                 215                 220
Leu Gly His Arg Asn Pro Gln Gly Leu Ala Phe Thr Pro Asn Gly Lys
225                 230                 235                 240
Leu Leu Gln Ser Glu Gln Gly Pro Asn Ser Asp Asp Glu Ile Asn Leu
                245                 250                 255
Ile Val Lys Gly Gly Asn Tyr Gly Trp Pro Asn Val Ala Gly Tyr Lys
            260                 265                 270
Asp Asp Ser Gly Tyr Ala Tyr Ala Asn Tyr Ser Ala Ala Asn Lys
        275                 280                 285
Ser Ile Lys Asp Leu Ala Gln Asn Gly Val Lys Val Ala Ala Gly Val
    290                 295                 300
Pro Val Thr Lys Glu Ser Glu Trp Thr Gly Lys Asn Phe Val Pro Pro
305                 310                 315                 320
Leu Lys Thr Leu Tyr Thr Val Gln Asp Thr Tyr Asn Tyr Asn Asp Pro
                325                 330                 335
Thr Cys Gly Glu Met Thr Tyr Ile Cys Trp Pro Thr Val Ala Pro Ser
            340                 345                 350
Ser Ala Tyr Val Tyr Lys Gly Gly Lys Lys Ala Ile Thr Gly Trp Glu
        355                 360                 365
Asn Thr Leu Leu Val Pro Ser Leu Lys Arg Gly Val Ile Phe Arg Ile
    370                 375                 380
Lys Leu Asp Pro Thr Tyr Ser Thr Thr Tyr Asp Asp Ala Val Pro Met
385                 390                 395                 400
Phe Lys Ser Asn Asn Arg Tyr Arg Asp Val Ile Ala Ser Pro Asp Gly
                405                 410                 415
Asn Val Leu Tyr Val Leu Thr Asp Thr Ala Gly Asn Val Gln Lys Asp
            420                 425                 430
Asp Gly Ser Val Thr Asn Thr Leu Glu Asn Pro Gly Ser Leu Ile Lys
        435                 440                 445
Phe Thr Tyr Lys Ala Lys
    450
```

```
<210> SEQ ID NO 2
<211> LENGTH: 1612
<212> TYPE: DNA
<213> ORGANISM: Acinetobacter calcoaceticus

<400> SEQUENCE: 2
agctactttt atgcaacaga gcctttcaga aatttagatt ttaatagatt cgttattcat      60
cataatacaa atcatataga gaactcgtac aaacccttta ttagaggttt aaaaattctc     120
ggaaaatttt gacaatttat aaggtggaca catgaataaa catttattgg ctaaaattgc     180
tttattaagc gctgttcagc tagttacact ctcagcattt gctgatgttc ctctaactcc     240
```

```
atctcaattt gctaaagcga atcagagaa cttttgacaag aaagttattc tatctaatct      300
aaataagccg catgctttgt tatggggacc agataatcaa atttggttaa ctgagcgagc      360
aacaggtaag attctaagag ttaatccaga gtcgggtagt gtaaaaacag tttttcaggt      420
accagagatt gtcaatgatg ctgatgggca gaatggttta ttaggttttg ccttccatcc      480
tgattttaaa aataatcctt atatctatat ttcaggtaca tttaaaaatc cgaaatctac      540
agataaagaa ttaccgaacc aaacgattat tcgtcgttat acctataata aatcaacaga      600
tacgctcgag aagccagtcg atttattagc aggattacct tcatcaaaag accatcagtc      660
aggtcgtctt gtcattgggc cagatcaaaa gatttattat acgattggtg accaagggcg      720
taaccagctt gcttatttgt tcttgccaaa tcaagcacaa catacgccaa ctcaacaaga      780
actgaatggt aaagactatc acacctatat gggtaaagta ctacgcttaa atcttgatgg      840
aagtattcca aaggataatc aagttttaa cggggtggtt agccatattt atacacttgg      900
acatcgtaat ccgcagggct tagcattcac tccaaatggt aaattattgc agtctgaaca      960
aggcccaaac tctgacgatg aaattaacct cattgtcaaa ggtggcaatt atggttggcc     1020
gaatgtagca ggttataaag atgatagtgg ctatgcttat gcaaattatt cagcagcagc     1080
caataagtca attaaggatt tagctcaaaa tggagtaaaa gtagccgcag gggtccctgt     1140
gacgaaagaa tctgaatgga ctggtaaaaa ctttgtccca ccattaaaaa ctttatatac     1200
cgttcaagat acctacaact ataacgatcc aacttgtgga gagatgacct acatttgctg     1260
gccaacagtt gcaccgtcat ctgcctatgt ctataagggc ggtaaaaaag caattactgg     1320
ttgggaaaat acattattgg ttccatcttt aaaacgtggt gtcattttcc gtattaagtt     1380
agatccaact tatagcacta cttatgatga cgctgtaccg atgtttaaga gcaacaaccg     1440
ttatcgtgat gtgattgcaa gtccagatgg gaatgtctta tatgtattaa ctgatactgc     1500
cggaaatgtc caaaaagatg atggctcagt aacaaataca ttagaaaacc caggatctct     1560
cattaagttc acctataagg ctaagtaata cagtcgcatt aaaaaaccga tc             1612
```

<210> SEQ ID NO 3
<211> LENGTH: 18
<212> TYPE: PRT
<213> ORGANISM: Acinetobacter calcoaceticus
<220> FEATURE:
<221> NAME/KEY: UNSURE
<222> LOCATION: 5
<223> OTHER INFORMATION: Xaa is any amino acid residue

<400> SEQUENCE: 3

Asn Leu Asp Gly Xaa Ile Pro Lys Asp Asn Pro Ser Phe Asn Gly Val
 1               5                  10                  15

Val Ser

<210> SEQ ID NO 4
<211> LENGTH: 36
<212> TYPE: PRT
<213> ORGANISM: Acinetobacter calcoaceticus
<220> FEATURE:
<221> NAME/KEY: UNSURE
<222> LOCATION: 24
<223> OTHER INFORMATION: Xaa is any amino acid residue
<221> NAME/KEY: UNSURE
<222> LOCATION: 25
<223> OTHER INFORMATION: Xaa is any amino acid residue

<400> SEQUENCE: 4

Gly Asp Gln Gly Arg Asn Gln Leu Ala Tyr Leu Phe Leu Pro Asn Gln

```
                1               5              10              15
          Ala Gln His Thr Pro Thr Gln Xaa Xaa Leu Asn Gly Lys Asp Tyr His
                           20                  25                  30

Thr Tyr Met Gly
                      35
```

<210> SEQ ID NO 5
<211> LENGTH: 10
<212> TYPE: PRT
<213> ORGANISM: Acinetobacter calcoaceticus
<220> FEATURE:
<221> NAME/KEY: UNSURE
<222> LOCATION: 9
<223> OTHER INFORMATION: Xaa is any amino acid residue
<221> NAME/KEY: UNSURE
<222> LOCATION: 10
<223> OTHER INFORMATION: Xaa is any amino acid residue

<400> SEQUENCE: 5

```
          Pro Thr Tyr Ser Thr Thr Tyr Asp Xaa Xaa
            1               5                  10
```

<210> SEQ ID NO 6
<211> LENGTH: 30
<212> TYPE: DNA
<213> ORGANISM: Artificial Sequence
<220> FEATURE:
<223> OTHER INFORMATION: primer for point mutation

<400> SEQUENCE: 6
cctttggaat atctccatca agatttaagc                                      30

<210> SEQ ID NO 7
<211> LENGTH: 30
<212> TYPE: DNA
<213> ORGANISM: Artificial Sequence
<220> FEATURE:
<223> OTHER INFORMATION: primer for point mutation

<400> SEQUENCE: 7
cctttggaat atgtccatca agatttaagc                                      30

<210> SEQ ID NO 8
<211> LENGTH: 30
<212> TYPE: DNA
<213> ORGANISM: Artificial Sequence
<220> FEATURE:
<223> OTHER INFORMATION: primer for point mutation

<400> SEQUENCE: 8
cctttggaat ttttccatca agatttaagc                                      30

<210> SEQ ID NO 9
<211> LENGTH: 30
<212> TYPE: DNA
<213> ORGANISM: Artificial Sequence
<220> FEATURE:
<223> OTHER INFORMATION: primer for point mutation

<400> SEQUENCE: 9
cctttggaat cattccatca agatttaagc                                      30

<210> SEQ ID NO 10
<211> LENGTH: 30
<212> TYPE: DNA
<213> ORGANISM: Artificial Sequence

```
-continued

<220> FEATURE:
<223> OTHER INFORMATION: primer for point mutation

<400> SEQUENCE: 10
cctttggaat agttccatca agatttaagc                              30

<210> SEQ ID NO 11
<211> LENGTH: 30
<212> TYPE: DNA
<213> ORGANISM: Artificial Sequence
<220> FEATURE:
<223> OTHER INFORMATION: primer for point mutation

<400> SEQUENCE: 11
cctttggaat atttccatca agatttaagc                              30

<210> SEQ ID NO 12
<211> LENGTH: 26
<212> TYPE: DNA
<213> ORGANISM: Artificial Sequence
<220> FEATURE:
<223> OTHER INFORMATION: primer for point mutation

<400> SEQUENCE: 12
caatgaggtt gaattcatcg tcagag                                  26

<210> SEQ ID NO 13
<211> LENGTH: 26
<212> TYPE: DNA
<213> ORGANISM: Artificial Sequence
<220> FEATURE:
<223> OTHER INFORMATION: primer for point mutation

<400> SEQUENCE: 13
gaccattcag ttcttttga gttggc                                   26

<210> SEQ ID NO 14
<211> LENGTH: 26
<212> TYPE: DNA
<213> ORGANISM: Artificial Sequence
<220> FEATURE:
<223> OTHER INFORMATION: primer for point mutation

<400> SEQUENCE: 14
gaccattcag tttttgttga gttggc                                  26

<210> SEQ ID NO 15
<211> LENGTH: 27
<212> TYPE: DNA
<213> ORGANISM: Artificial Sequence
<220> FEATURE:
<223> OTHER INFORMATION: primer for point mutation

<400> SEQUENCE: 15
acatcggtac agctttatca taagtag                                 27

<210> SEQ ID NO 16
<211> LENGTH: 27
<212> TYPE: DNA
<213> ORGANISM: Artificial Sequence
<220> FEATURE:
<223> OTHER INFORMATION: primer for point mutation

<400> SEQUENCE: 16
acatcggtac atcgtcatca taagtag                                 27
```

GLUCOSE DEHYDROGENASE

This application is the national phase under 35 U.S.C. § 371 of PCT International Application No. PCT/JP00/02322 which has an International filing date of Apr. 10, 2000, which designated the United States of America.

TECHNICAL FIELD

The present invention relates to the preparation of glucose dehydrogenases having pyrrolo-quinoline quinone as a coenzyme (PQQGDH) and their use for glucose assays.

BACKGROUND ART

Blood glucose is an important marker for diabetes. In the fermentative production using microorganisms, glucose levels are assayed for monitoring the process. Conventional glucose assays were based on enzymatic methods using a glucose oxidase (GOD) or glucose-6-phosphate dehydrogenase (G6PDH). However, GOD-based assays required addition of a catalase or peroxidase to the assay system in order to quantitate the hydrogen peroxide generated by glucose oxidation reaction. G6PDHs have been used for spectrophotometric glucose assays, in which case a coenzyme NAD(P) had to be added to the reaction system.

An object of the present invention is to provide a modified water-soluble PQQGDH with improved thermal stability.

DISCLOSURE OF THE INVENTION

We found that PQQGDHs with high stability are useful as novel enzymes alternative to the enzymes that have been used for enzymatic glucose assays. PQQGDHs are useful as recognition elements of glucose sensors because they have high oxidation activity for glucose and they are coenzyme-bound enzymes that require no oxygen as an electron acceptor.

PQQGDHs catalyze the reaction in which glucose is oxidized to produce gluconolactone. PQQGDHs include membrane-bound enzymes and water-soluble enzymes. Membrane-bound PQQGDHs are single peptide proteins having a molecular weight of about 87 kDa and widely found in various gram-negative bacteria. Water-soluble PQQGDHs have been identified in several strains of *Acinetobacter calcoaceticus* (Biosci. Biotech. Biochem. (1995), 59(8), 1548–1555), and their structural genes were cloned to show the amino acid sequences (Mol. Gen. Genet. (1989), 217:430–436). The water-soluble PQQGDH derived from *A. calcoaceticus* is a homodimer having a molecular weight of about 50 kDa.

Recently, a Dutch group made an X-ray crystal structure analysis of the water-soluble PQQGDH to show the higher-order structure of the enzyme (J. Mol. Biol., 289, 319–333 (1999), The crystal structure of the apo form of the soluble quinoprotein glucose dehydrogenase from *Acinetobacter calcoaceticus* reveals a novel internal conserved sequence repeat; A. Oubrie et al., The EMBO Journal, 18(19) 5187–5194 (1999), Structure and mechanism of soluble quinoprotein glucose dehydrogenase, A. Oubrie et al., PNAS, 96(21), 11787–11791 (1999), Active-site structure of the soluble quinoprotein glucose dehydrogenase complexed with methylhydrazine; A covalent cofactor-inhibitor complex, A. Oubrie et al.). These papers showed that the water-soluble PQQGDH is a β-propeller protein composed of six W-motifs (FIG. 7).

As a result of careful studies to develop a modified PQQGDH that can be applied to clinical tests or food analyses by improving the conventional water-soluble PQQGDH to increase the thermal stability, we succeeded in obtaining an enzyme with very high stability by introducing an amino acid change into a specific region of the water-soluble PQQGDH.

Accordingly, the present invention provides a modified glucose dehydrogenase having pyrrolo-quinoline quinone as a coenzyme wherein an amino acid residue corresponding to serine 231 or glutamine 209 or glutamate 210 or aspartate 420 or alanine 421 in the water-soluble PQQGDH derived from *Acinetobacter calcoaceticus* (hereinafter also referred to as the wild-type PQQGDH) is replaced by another amino acid residue. As used herein, the "modified glucose dehydrogenase" means a glucose dehydrogenase wherein at least one amino acid residue in a naturally occurring glucose dehydrogenase is replaced by another amino acid residue. The amino acid numbering herein starts from the initiator methionine as the +1 position.

The present invention also provides a modified glucose dehydrogenase having pyrrolo-quinoline quinone as a coenzyme wherein at least one amino acid residue is replaced by another amino acid residue in one or more regions selected from the group consisting of the regions defined by residues 48–53, 60–62, 69–71, 79–82, 91–101, 110–115, 127–135, 147–150, 161–169, 177–179, 186–221, 227–244, 250–255, 261–263, 271–275, 282–343, 349–377, 382–393, 400–403, 412–421, 427–432, 438–441 and 449–468 in the amino acid sequence shown as SEQ ID NO: 1, characterized in that it has higher thermal stability than that of the water-soluble PQQGDH derived from *Acinetobacter calcoaceticus*. Preferably, the modified PQQGDH of the present invention has a residual activity that is higher than the residual activity of the wild-type PQQGDH by 10% or more, more preferably 20% or more, still more preferably 30% or more after heat treatment at 50° C. for 10 minutes. Preferably, the modified PQQGDH of the present invention has a heat inactivation half-life that is longer than the heat inactivation half-life of the wild-type PQQGDH by 5 minutes or more, more preferably 15 minutes or more at 55° C. In especially preferred modified PQQGDHs of the present invention, at least one amino acid residue is replaced by another amino acid residue in the region defined by residues 227–244, 186–221 or 412–421 in the amino acid sequence shown as SEQ ID NO: 1. In still more preferred modified PQQGDHs of the present invention, serine 231 is replaced by an amino acid residue selected from the group consisting of lysine, asparagine, aspartate, histidine, methionine, leucine and cysteine, or glutamine 209 is replaced by lysine, or glutamate 210 is replaced by lysine, or aspartate 420 is replaced by lysine, or alanine 421 is replaced by aspartate in the amino acid sequence shown as SEQ ID NO: 1.

In another aspect, modified PQQGDHs of the present invention comprise the sequence:

Asn Leu Asp Gly Xaa231 Ile Pro Lys Asp Asn Pro Ser Phe Asn Gly Val Val Ser (SEQ ID NO: 3)

wherein Xaa231 represents a natural amino acid residue other than Ser;

or the sequence:

Gly Asp Gln Gly Arg Asn Gln Leu Ala Tyr Leu Phe Leu Pro Asn Gln Ala Gln His Thr Pro Thr Gln Xaa209 Xaa210 Leu Asn Gly Lys Asp Tyr His Thr Tyr Met Gly (SEQ ID NO: 4)

wherein Xaa209 and Xaa210 represent any natural amino acid residue, provided that when Xaa209 represents Gln, Xaa 210 does not represent Glu;

or the sequence:

Pro Thr Tyr Ser Thr Thr Tyr Asp Xaa420 Xaa421 (SEQ ID NO: 5)

wherein Xaa420 and Xaa421 represent any natural amino acid residue, provided that when Xaa420 represents Asp, Xaa421 does not represent Ala.

The present invention also provides a gene encoding any of the modified glucose dehydrogenases described above, a vector containing said gene and a transformant containing said gene, as well as a glucose assay kit and a glucose sensor comprising a modified glucose dehydrogenase of the present invention.

Enzyme proteins of modified PQQGDHs of the present invention have high thermal stability and high oxidation activity for glucose so that they can be applied to highly sensitive and highly selective glucose assays. Especially, they are expected to provide the advantages that the enzymes can be produced at high yield with less inactivation during preparation/purification; the enzymes can be easily stored because of their high stability in solutions; the enzymes can be used to prepare an assay kit or an enzyme sensor with less inactivation; and the assay kit or enzyme sensor prepared with the enzymes has excellent storage properties because of the high thermal stability.

BRIEF DESCRIPTION OF THE DRAWINGS

FIG. 4 shows substrate specificities of modified enzymes of the present invention.

THE MOST PREFERRED EMBODIMENTS OF THE INVENTION

Structure of Modified PQQGDHs

Figure 1:
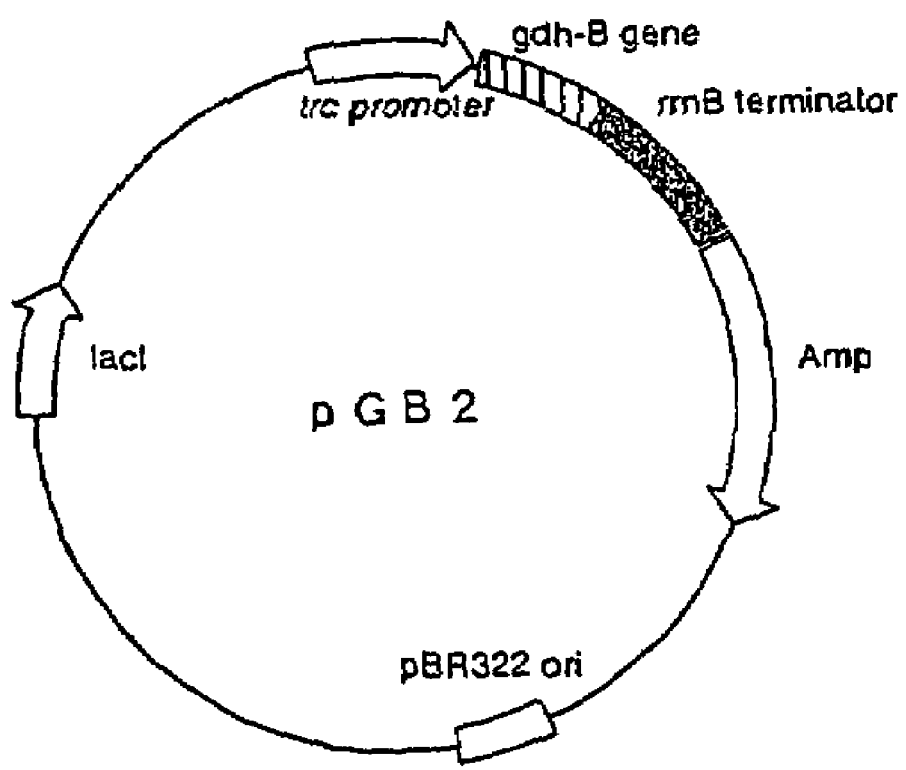
FIG. 1 shows the structure of the plasmid pGB2 used in the present invention.

We introduced random mutations into the coding region of the gene encoding the water-soluble PQQGDH by error-prone PCR to construct a library of water-soluble PQQGDHs carrying amino acid changes. These genes were transformed into *E. coli* and screened for the residual activity of the PQQGDHs after heat treatment to give a number of clones that express PQQGDHs with improved thermal stability.

Analysis of the nucleotide sequence of one of these clones showed that Ser 231 had been changed to Cys. When this amino acid residue was replaced by various other amino acid residues, mutant enzymes with higher thermal stability than that of the wild type water-soluble PQQGDH were obtained in every case.

The water-soluble PQQGDH has the structure of β-propeller protein composed of six W-motifs. In the present invention, it was found that thermal stability is improved by replacing Ser 231 in the loop region defined by residues 227–244 by another amino acid residue. Then, site-specific mutations were introduced into other loop regions to try to improve the thermal stability. Mutant enzymes carrying Gln209Lys or Glu210Lys in the loop defined by residues 186–221 or Asp420Lys or Ala421Asp in the loop defined by residues 412–421 showed improved thermal stability.

Thus, it was demonstrated that water-soluble PQQGDHs with improved thermal stability can be constructed by introducing a proper change into a loop region according to the present invention. This is probably because the interaction between the loop regions connecting W-motifs contributes to the stabilization of the structure of the β-propeller protein in water-soluble PQQGDHs. The residues Ser231, Gln209, Gly210, Asp420 and Ala421 shown above are only illustrative but not limiting the present invention. The present invention first showed in the art that thermal stability of PQQGDHs can be improved by introducing a change into a specific site of the structural gene in a loop region, thereby providing here a methodology for improving thermal stability of PQQGDHs.

Modified PQQGDHs of the present invention are characterized in that they contain an amino acid residue change in a specific region in the amino acid sequence of the wild-type PQQGDH shown as SEQ ID NO: 1. Accordingly, the present invention provides a modified glucose dehydrogenase having pyrrolo-quinoline quinone as a coenzyme wherein at least one amino acid residue is replaced by another amino acid residue in one or more regions selected from the group consisting of the regions defined by residues 48–53, 60–62, 69–71, 79–82, 91–101, 110–115, 127–135, 147–150, 161–169, 177–179, 186–221, 227–244, 250–255, 261–263, 271–275, 282–343, 349–377, 382–393, 400–403, 412–421, 427–432, 438–441 and 449–468 in the amino acid sequence shown as SEQ ID NO: 1.

In preferred modified PQQGDHs of the present invention, at least one amino acid residue is replaced by another amino acid residue in the region defined by residues 227–244, 186–221 or 412–421 in the amino acid sequence shown as SEQ ID NO: 1. In especially preferred modified PQQGDHs of the present invention, serine 231 is replaced by an amino acid residue selected from the group consisting of lysine, asparagine, aspartate, histidine, methionine, leucine and cysteine, or glutamine 209 is replaced by lysine, or glutamate 210 is replaced by lysine, or aspartate 420 is replaced by lysine, or alanine 421 is replaced by aspartate in the amino acid sequence shown as SEQ ID NO: 1.

In another aspect, modified PQQGDHs of the present invention comprise the sequence:

Asn Leu Asp Gly Xaa231 Ile Pro Lys Asp Asn Pro Ser Phe Asn Gly Val Val Ser (SEQ ID NO: 3)

wherein Xaa231 represents a natural amino acid residue other than Ser;

or the sequence:

Gly Asp Gln Gly Arg Asn Gln Leu Ala Tyr Leu Phe Leu Pro Asn Gln Ala Gln His Thr Pro Thr Gln Xaa209 Xaa210 Leu Asn Gly Lys Asp Tyr His Thr Tyr Met Gly (SEQ ID NO: 4)

wherein Xaa209 and Xaa210 represent any natural amino acid residue, provided that when Xaa209 represents Gln, Xaa 210 does not represent Glu;

or the sequence:

Pro Thr Tyr Ser Thr Thr Tyr Asp Xaa420 Xaa421 (SEQ ID NO: 5)

wherein Xaa420 and Xaa421 represent any natural amino acid residue, provided that when Xaa420 represents Asp, Xaa 421 does not represent Ala.

In modified glucose dehydrogenases of the present invention, other amino acid residues may be partially deleted or substituted or other amino acid residues may be added so far as glucose dehydrogenase activity is retained. Various techniques for such deletion, substitution or addition of amino acid residues are known in the art as described in Sambrook et al., "Molecular Cloning: A Laboratory Manual", Second Edition, 1989, Cold Spring Harbor Laboratory Press, New York, for example. Those skilled in the art can readily test whether or not a glucose dehydrogenase containing such deletion, substitution or addition has a desired glucose dehydrogenase activity according to the teaching herein. Those skilled in the art can also predict a region having a loop structure in water-soluble PQQGDHs derived from other bacteria according to the teaching herein and replace an amino acid residue in this region to obtain modified glucose dehydrogenases with improved thermal stability. Particularly, an amino acid residue corresponding to serine 231, glutamine 209, glutamate 210, aspartate 420 or alanine 421 in the water-soluble PQQGDH derived from *Acinetobacter calcoaceticus* can be readily identified by comparing the primary structures of proteins in alignment, so that modified glucose dehydrogenases can be obtained by replacing such a residue by another amino acid residue according to the present invention. These modified glucose dehydrogenases are also within the scope of the present invention.

Process for Preparing Modified PQQGDHs

The sequence of the gene encoding the wild-type water-soluble PQQGDH derived from *Acinetobacter calcoaceticus* is defined by SEQ ID NO: 2.

Genes encoding modified PQQGDHs of the present invention can be constructed by replacing the nucleotide sequence encoding an amino acid residue occurring in a loop region as described above in the gene encoding the wild-type water-soluble PQQGDH by the nucleotide sequence encoding an amino acid residue to be substituted. Various techniques for such site-specific nucleotide sequence substitution are known in the art as described in Sambrook et al., "Molecular Cloning: A Laboratory Manual", Second Edition, 1989, Cold Spring Harbor Laboratory Press, New York, for example. Thus obtained mutant gene is inserted into a gene expression vector (for example, a plasmid) and transformed into an appropriate host (for example, *E. coli*). A number of vector/host systems for expressing a foreign protein are known and various hosts such as bacteria, yeasts or cultured cells are suitable.

Random mutations are introduced by error-prone PCR into a target loop region to construct a gene library of modified water-soluble PQQGDHs carrying mutations in the loop region. These genes are transformed into *E. coli* to screen each clone for the thermal stability of the PQQGDH. Water-soluble PQQGDHs are secreted into the periplasmic space when they are expressed in *E. coli*, so that they can be easily assayed for enzyme activity using the *E. coli* cells. This library is heated at 60–70° C. for about 30 minutes and then combined with glucose and a PMS-DCIP dye to visually determine the residual PQQGDH activity so that clones showing residual activity even after heat treatment are selected and analyzed for the nucleotide sequence to confirm the mutation.

Thus obtained transformed cells expressing modified PQQGDHs are cultured and harvested by centrifugation or other means from the culture medium, and then disrupted with a French press or osmotically shocked to release the periplasmic enzyme into the medium. The enzyme may be ultracentrifuged to give a water-soluble PQQGDH-containing fraction. Alternatively, the expressed PQQGDH may be secreted into the medium by using an appropriate host/vector system. The resulting water-soluble fraction is purified by ion exchange chromatography, affinity chromatography, HPLC and the like to prepare a modified PQQGDH of the present invention.

Method for Assaying Enzyme Activity

PQQGDHs of the present invention associate with PQQ as a coenzyme in catalyzing the reaction in which glucose is oxidized to produce gluconolactone.

The enzyme activity can be assayed by using the color-developing reaction of a redox dye to measure the amount of PQQ reduced with PQQGDH-catalyzed oxidation of glucose. Suitable color-developing reagents include PMS (phenazine methosulfate)-DCIP (2,6-dichlorophenolindophenol), potassium ferricyanide and ferrocene, for example.

Thermal Stability

Thermal stability of modified PQQGDHs of the present invention can be evaluated by incubating the enzyme of interest at a high temperature (for example, 55° C.), sampling aliquots at regular intervals and assaying the enzyme activity to monitor the decrease in the enzyme activity with time. Typically, thermal stability of an enzyme is expressed as a heat inactivation half-life, i.e. the time required for the enzyme activity to be reduced to 50% ($t_{1/2}$). Alternatively, thermal stability can also be expressed as the residual enzyme activity after heat treatment of the enzyme for a given period (the ratio of the activity after heat treatment to the activity before heat treatment).

Modified PQQGDHs of the present invention are characterized by higher thermal stability than that of the wild-type PQQGDH. Thus, they have the advantages that the enzymes can be produced at high yield with less inactivation during preparation/purification; the enzymes can be easily stored because of their high stability in solutions; the enzymes can be used to prepare an assay kit or an enzyme sensor with less inactivation; and the assay kit or enzyme sensor prepared with the enzymes has excellent storage properties because of the high thermal stability.

Glucose Assay Kit

The present invention also relates to a glucose assay kit comprising a modified PQQGDH according to the present invention. The glucose assay kit of the present invention comprises a modified PQQGDH according to the present invention in an amount enough for at least one run of assay. In addition to the modified PQQGDH according to the present invention, the kit typically comprises a necessary buffer for the assay, a mediator, standard glucose solutions for preparing a calibration curve and instructions. Modified PQQGDHs according to the present invention can be provided in various forms such as freeze-dried reagents or solutions in appropriate preservative solutions. Modified PQQGDHs according to the present invention are preferably provided in the form of a holoenzyme, though they may also be provided as an apoenzyme and converted into a holoenzyme before use.

Glucose Sensor

The present invention also relates to a glucose sensor using a modified PQQGDH according to the present invention. Suitable electrodes include carbon, gold, platinum and the like electrodes, on which an enzyme of the present invention is immobilized by using a crosslinking agent; encapsulation in a polymer matrix; coating with a dialysis membrane; using a photo-crosslinkable polymer, an electrically conductive polymer or a redox polymer; fixing the enzyme in a polymer or adsorbing it onto the electrode with an electron mediator including ferrocene or its derivatives; or any combination thereof. Modified PQQGDHs of the present invention are preferably immobilized in the form of a holoenzyme on an electrode, though they may be immobilized as an apoenzyme and PQQ may be provided as a separate layer or in a solution. Typically, modified PQQGDHs of the present invention are immobilized on a carbon electrode with glutaraldehyde and then treated with an amine-containing reagent to block glutaraldehyde.

Glucose levels can be measured as follows. PQQ, CaCl$_2$ and a mediator are added to a thermostat cell containing a buffer and kept at a constant temperature. Suitable mediators include, for example, potassium ferricyanide and phenazine methosulfate. An electrode on which a modified PQQGDH of the present invention has been immobilized is used as a working electrode in combination with a counter electrode (e.g. a platinum electrode) and a reference electrode (e.g. an Ag/AgCl electrode). After a constant voltage is applied to the carbon electrode to reach a steady current, a glucose-containing sample is added to measure the increase in current. The glucose level in the sample can be calculated from a calibration curve prepared with glucose solutions at standard concentrations.

The disclosures of all the patents and documents cited herein are entirely incorporated herein as reference. The present application claims priority based on Japanese Patent Applications Nos. 1999-101143 and 2000-9152, the disclosure of which is entirely incorporated herein as reference.

The following examples further illustrate the present invention without, however, limiting the same thereto.

EXAMPLE 1

Construction and Screening of a Mutant PQQGDH Gene Library:

The plasmid pGB2 was obtained by inserting the structural gene encoding the PQQGDH derived from *Acinetobacter* calcoaceticus into the multicloning site of the vector pTrc99A (Pharmacia) (FIG. 1). This plasmid was used as a template to introduce random mutations into the coding region by error-prone PCR. The PCR reaction was carried out in a solution having the composition shown in Table 1 under the conditions of 94° C. for 3 minutes, 30 cycles of 94° C. for 3 minutes, 50° C. for 2 minutes and 72° C. for 2 minutes, and finally 72° C. for 10 minutes.

TABLE 1

| | |
|---|---|
| TaqDNA polymerase (5U/µl) | 0.5 µl |
| Template DNA | 1.0 µl |
| Forward primer ABF | 4.0 µl |
| Reverse primer ABR | 4.0 µl |
| 10 × Taq polymerase buffer | 10.0 µl |
| 1M β-mercaptoethanol | 1.0 µl |
| DMSO | 10.0 µl |
| 5 mM MnCl$_2$ | 10.0 µl |
| 10 mM dGTP | 2.0 µl |
| 2 mM dATP | 2.0 µl |
| 10 mM dCTP | 2.0 µl |
| 10 mM dTTP | 2.0 µl |
| H$_2$O | 51.5 µl |
| | 100.0 µl |

The resulting mutant water-soluble PQQGDH library was transformed into *E. coli* and each colony formed was transferred to a microtiter plate. After heating the plate at 60° C. for about 30 minutes, glucose and PMS-DCIP were added and the residual PQQGDH activity was visually evaluated. A number of clones showing PQQGDH activity even after heat treatment were obtained.

One of these clones was randomly selected and analyzed for the nucleotide sequence to show that serine 231 had been changed to cysteine.

EXAMPLE 2

Figure 2:
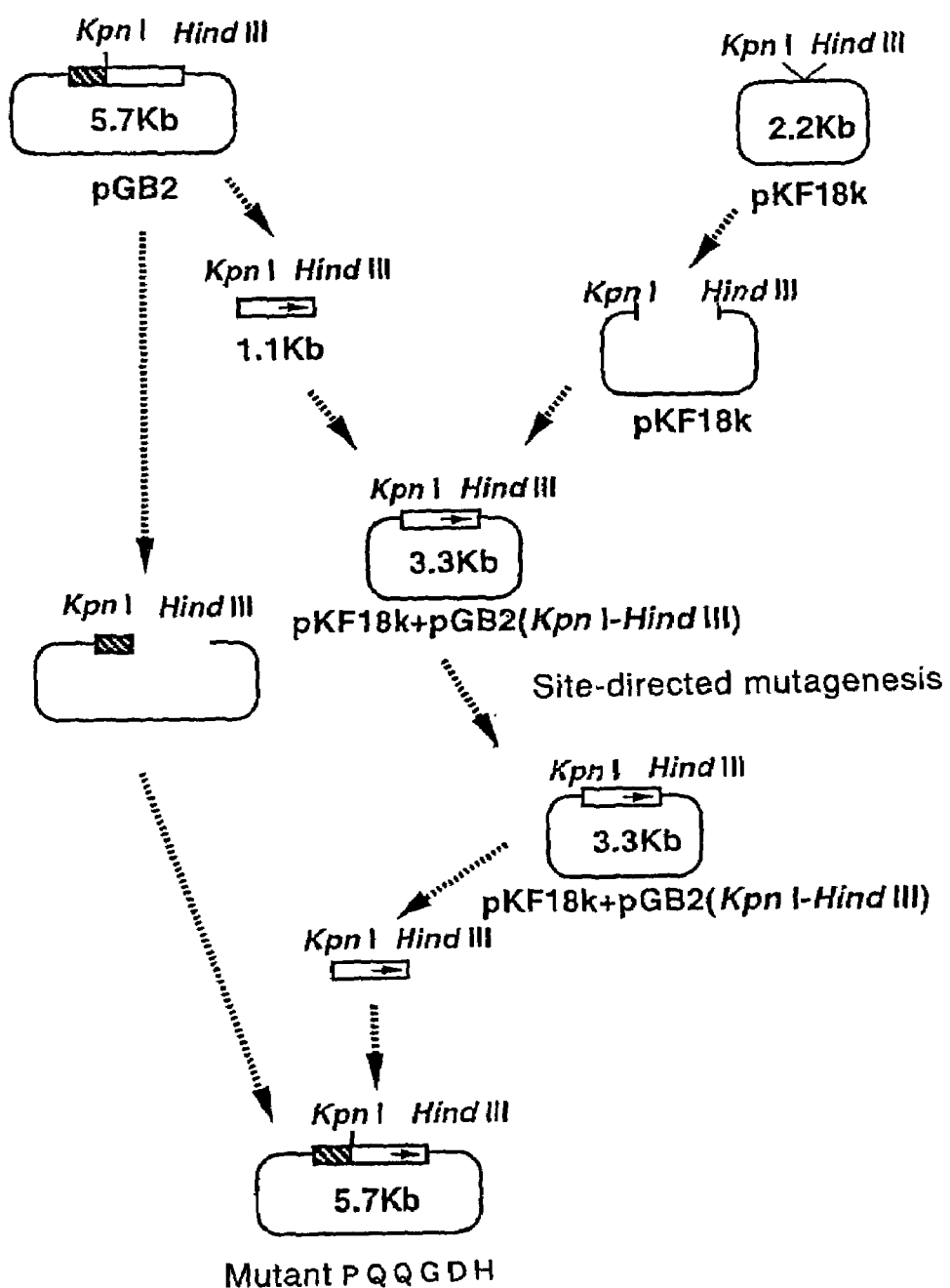
FIG. 2 shows a scheme for preparing a mutant gene encoding a modified enzyme of the present invention.

Construction of Modified PQQGDH Genes:

Based on the structural gene of the PQQGDH derived from *Acinetobacter calcoaceticus* shown as SEQ ID NO: 2, the nucleotide sequence encoding serine 231, glutamine 209, aspartate 420 or alanine 421 was replaced by the nucleotide sequences encoding given amino acid residues by site-directed mutagenesis according to a standard method as shown in FIG. 2 using the plasmid pGB2. Table 2 shows the sequences of the synthetic oligonucleotide target primers used for mutagenesis. In Table 2, "S231D" means that serine 231 is replaced by aspartate, for example.

TABLE 2

(SEQ ID NOS: 6–16)

S231D
5'-C CTT TGG AAT ATC TCC ATC AAG ATT TAA GC-3'

S231H
5'-C CTT TGG AAT ATG TCC ATC AAG ATT TAA GC-3'

S231K
5'-C CTT TGG AAT TTT TCC ATC AAG ATT TAA GC-3'

S231L
5'-C CTT TGG AAT CAT TCC ATC AAG ATT TAA GC-3'

S231M
5'-C CTT TGG AAT ACT TCC ATC AAG ATT TAA GC-3'

S231N
5'-C CTT TGG AAT ATT TCC ATC AAG ATT TAA GC-3'

I278F
5'-C AAT GAG GTT GAA TTC ATC GTC AGA G-3'

Q209K
5'-C ACC ATT CAG TTC TTT TTG AGT TGG C-3'

E210K
5'-C ACC ATT CAG TTT TTG TTG AGT TGG C-3'

D420K
5'-A CAT CGG TAC AGC TTT ATC ATA AGT AG-3'

A421D
5'-A CAT CGG TAC ATC GTC ATC ATA AGT AG-3'

A KpnI-HindIII fragment containing a part of the gene encoding the PQQGDH derived from *Acinetobacter* calcoaceticus was integrated into the vector plasmid pKF18k (Takara Shuzo Co., Ltd.) and used as a template. Fifty fmols of this template, 5 pmol of the selection primer attached to the Mutan™-Express Km Kit (Takara Shuzo Co., Ltd.) and 50 pmol of the phosphorylated target primer were mixed with the annealing buffer attached to the kit in an amount equivalent to 1/10 of the total volume (20 µl), and the mixture was heated at 100° C. for 3 minutes to denature the plasmid into a single strand. The selection primer serves for reversion of dual amber mutations on the kanamycin-resistance gene of pKF18k. The mixture was placed on ice for 5 minutes to anneal the primers. To this mixture were added 3 µl of the extension buffer attached to the kit, 1 µl of T4 DNA ligase, 1 µl of T4 DNA polymerase and 5 µl of sterilized water to synthesize a complementary strand.

The synthetic strand was transformed into a DNA mismatch repair-deficient strain *E. coli* BMH71-18mutS and shake-cultured overnight to amplify the plasmid.

Then, the plasmid copies were extracted from the cultures and transformed into *E. coli* MV1184 and then extracted from the colonies. These plasmids were sequenced to confirm the introduction of the intended mutations. These fragments were substituted for the KpnI-HindIII fragment of the gene encoding the wild-type PQQGDH on the plasmid pGB2A to construct genes for modified PQQGDHs.

EXAMPLE 3

Preparation of Modified Enzymes:

The gene encoding the wild-type or each modified PQQGDH was inserted into the multicloning site of an *E. coli* expression vector pTrc99A (Pharmacia), and the resulting plasmid was transformed into the *E. coli* strain DH5α. The transformant was shake-cultured at 37° C. overnight on 450 ml of L medium (containing 50 μg/ml of ampicillin) in a Sakaguchi flask, and inoculated on 7 l of L medium containing 1 mM $CaCl_2$ and 500 μM PQQ. About 3 hours after starting cultivation, isopropyl thiogalactoside was added at a final concentration of 0.3 mM, and cultivation was further continued for 1.5 hours. The cultured cells were harvested from the medium by centrifugation (5,000×g, 10 min, 4° C.), and washed twice with a 0.85% NaCl solution. The collected cells were disrupted with a French press, and centrifuged (10,000×g, 15 min, 4° C.) to remove undisrupted cells. The supernatant was ultracentrifuged (160,500×g (40,000 r.p.m.), 90 min, 4° C.) to give a water-soluble fraction, which was used in the subsequent examples as a crude enzyme sample.

Thus obtained water-soluble fraction was further dialyzed against 10 mM phosphate buffer, pH 7.0 overnight. The dialyzed sample was adsorbed to a cation chromatographic column TSKgel CM-TOYOPEARL 650M (Tosoh Corp.), which had been equilibrated with 10 mM phosphate buffer, pH 7.0. This column was washed with 750 ml of 10 mM phosphate buffer, pH 7.0 and then the enzyme was eluted with 10 mM phosphate buffer, pH 7.0 containing 0–0.2 M NaCl at a flow rate of 5 ml/min. Fractions having GDH activity were recovered and dialyzed against 10 mM MOPS-NAOH buffer, pH 7.0 overnight. Thus, an electrophoretically homogeneous modified PQQGDH protein was obtained. This was used in the subsequent examples as a purified enzyme sample.

EXAMPLE 4

Assay of Enzyme Activity:

Enzyme activity was assayed by using PMS (phenazine methosulfate)-DCIP (2,6-dichlorophenolindophenol) in 10 mM MOPS-NaOH buffer (pH 7.0) to monitor changes in the absorbance of DCIP at 600 nm with a spectrophotometer and expressing the reaction rate of the enzyme as the rate of decrease in the absorbance. The enzyme activity for reducing 1 μmol of DCIP in 1 minute was 1 U. The molar extinction coefficient of DCIP at pH 7.0 was 16.3 $mM^{-1}$.

EXAMPLE 5

Evaluation of Thermal Stability of Crude Enzyme Samples:

Each of the crude enzyme samples of the wild-type and modified PQQGDHs obtained in Example 3 was converted into a holoenzyme in the presence of 1 μM PQQ and 1 mM $CaCl_2$ for 1 hour or longer and then incubated at 55° C. Aliquots were sampled at regular intervals and rapidly cooled on ice. These samples were assayed for the enzyme activity by the method of Example 4 to determine the time required for reducing the activity to 50% ($t_{1/2}$).

The results are shown in Table 3.

TABLE 3

|  | $t_{1/2}$ (min) |
| --- | --- |
| Wild type | 10 |
| S231K | 95 |
| S231L | 16 |
| S231D | 25 |
| S231C | 50 |
| S231M | 14 |
| S231H | 15 |
| S231N | 50 |
| I278F | 25 |
| Q209K | 40 |
| E210K | 40 |
| D420K | 20 |
| A421D | 80 |

All the modified PQQGDHs of the present invention have a heat inactivation half-life at 55° C. longer than that of the wild-type PQQGDH, showing that they have higher thermal stability than that of the wild-type PQQGDH.

EXAMPLE 6

Evaluation of Thermal Stability of Purified Enzyme Samples:

The purified samples of the wild-type enzyme and the modified enzyme S231K obtained in Example 3 were measured for the heat inactivation half-life at 55° C. in the same manner as in Example 5. The purified samples of the wild-type enzyme and the modified enzyme S231K had half-lives of 5 minutes and 41 minutes, respectively.

Then, each of the purified samples of the wild-type enzyme and the modified enzyme S231K obtained in Example 3 was converted into a holoenzyme in the presence of 1 μM PQQ and 1 mM $CaCl_2$ for 1 hour or longer. Then, each sample was incubated at a given temperature in 10 mM MOPS buffer (pH 7.0) containing 1 μM PQQ and 1 mM $CaCl_2$ for 10 minutes, and then rapidly cooled on ice. These samples were assayed for the enzyme activity by the method of Example 4 to determine the residual activity relative to the activity before heat treatment.

Figure 3:
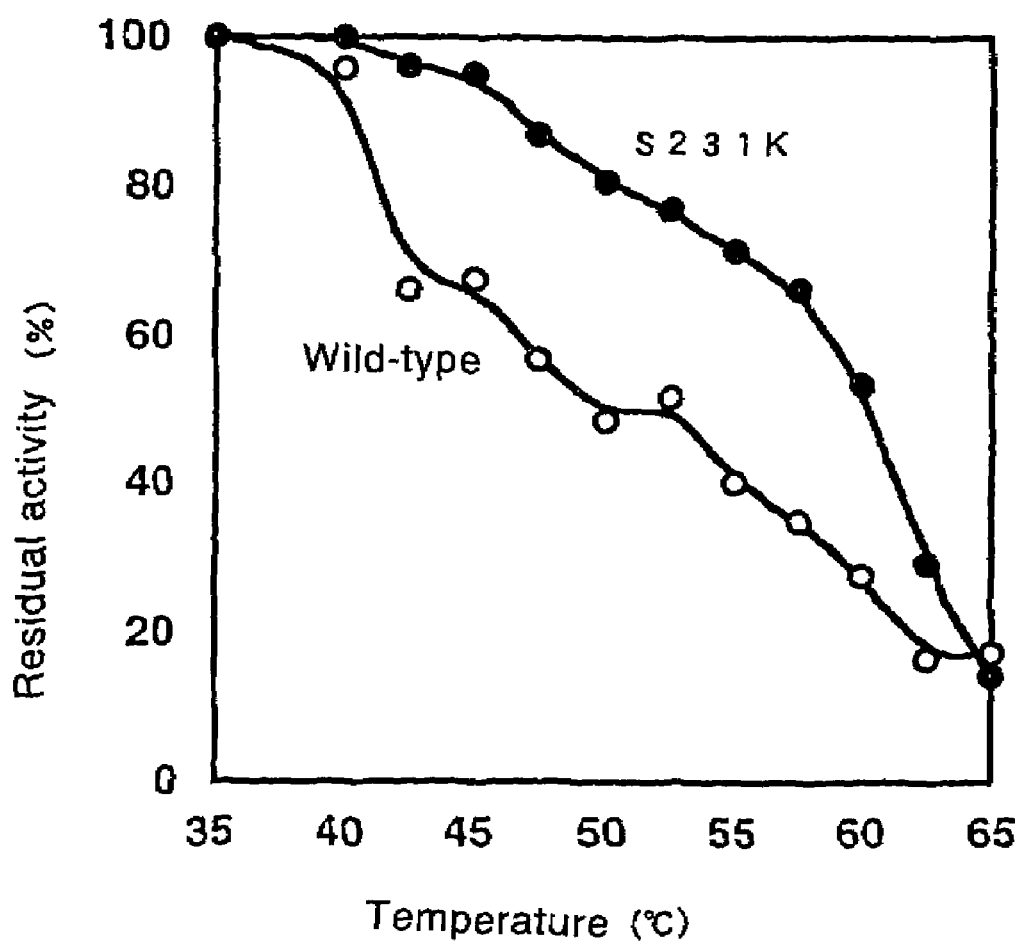
FIG. 3 shows thermal stability of a modified enzyme of the present invention.

The results are shown in FIG. 3. The modified enzyme S231K had higher activities than those of the wild-type enzyme at various temperatures of 40–62.5° C.

EXAMPLE 7

Evaluation of Enzyme Activity:

The crude enzyme sample of the modified enzyme S231K obtained in Example 3 was converted into a holoenzyme in the presence of 1 μM PQQ and 1 mM $CaCl_2$ for 1 hour or longer. A 187 μl-aliquot was combined with 3 μl of an activating reagent (prepared from 48 μl of 6 mM DCIP, 8 μl of 600 mM PMS and 16 μl of 10 mM phosphate buffer, pH 7.0) and 10 μl of glucose solutions at various concentrations, and assayed for the enzyme activity at room temperature by the method shown in Example 4. The Km and Vmax were determined by plotting the substrate concentration vs. enzyme activity. The S231K variant had a Km value for glucose of about 20 mM and a Vmax value of 3300 U/mg. The Km value of the wild-type PQQGDH for glucose reported to date was about 20 mM with the Vmax value being 2500–7000 U/mg depending on the measurement conditions. These results show that the modified PQQGDH S231K has high activity comparable to that of the wild-type PQQGDH.

EXAMPLE 8

Evaluation of Substrate Specificity:

Crude samples of various modified enzymes were tested for substrate specificity. The substrates tested were glucose, 2-deoxy-D-glucose, mannose, allose, 3-o-methyl-D-glucose, galactose, xylose, lactose and maltose, and each sample was incubated with 20 mM of each substrate for 30 minutes in the presence of 1 μM PQQ and 1 mM CaCl$_2$ and assayed for the enzyme activity in the same manner as in Example 7 to determine the relative activity to the activity for glucose. As shown in FIG. 4, all the modified enzymes of the present invention showed a similar substrate specificity to that of the wild-type enzyme.

EXAMPLE 9

Figure 5:
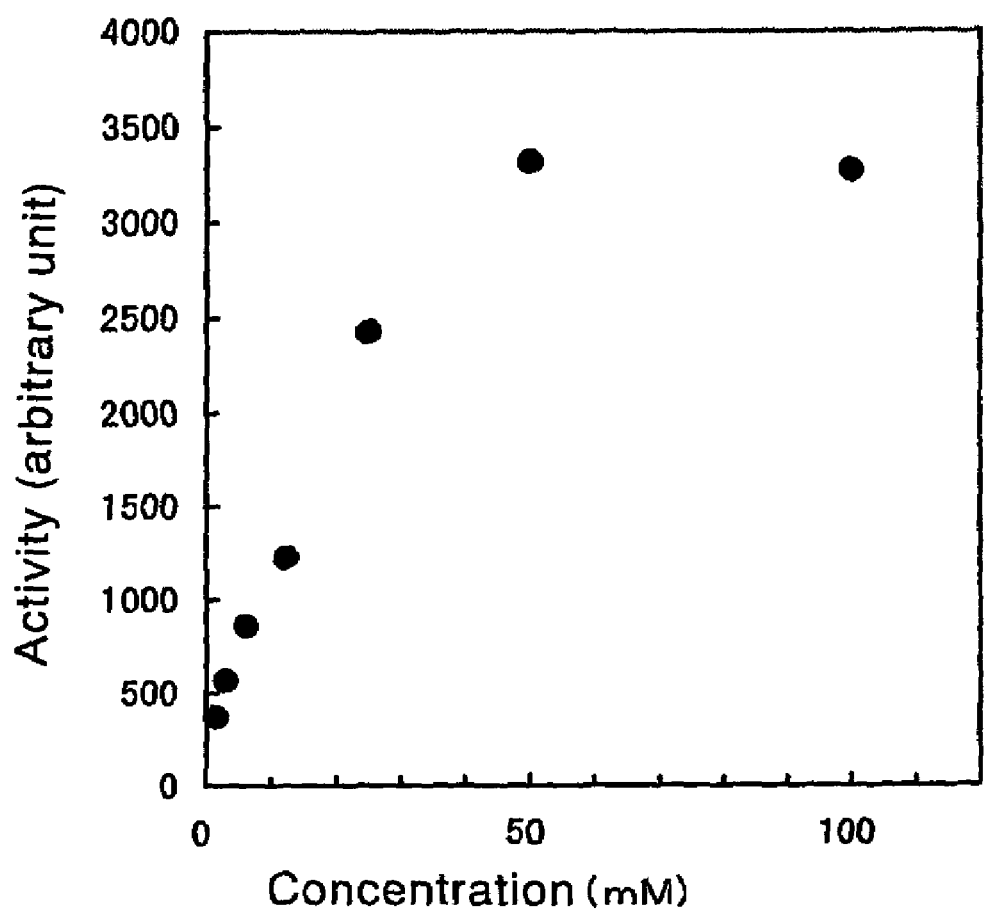
FIG. 5 shows a glucose assay using a modified PQQGDH of the present invention.

Glucose Assay:

A modified PQQGDH was used for assaying glucose. The modified enzyme S231K was converted into a holoenzyme in the presence of 1 μM PQQ and 1 mM CaCl$_2$ for 1 hour or longer, and assayed for the enzyme activity in the presence of glucose at various concentrations as well as 5 μM PQQ and 10 mM CaCl$_2$ by the method described in Example 4 based on changes of the absorbance of DCIP at 600 nm. As shown in FIG. 5, the modified PQQGDH S231K can be used for assaying glucose in the range of 5 mM–50 mM.

EXAMPLE 10

Preparation and Evaluation of an Enzyme Sensor:

Five units of the modified enzyme S231K was freeze-dried with 20 mg of carbon paste. After thorough mixing, the mixture was applied only on the surface of a carbon paste electrode preliminarily filled with about 40 mg of carbon paste and polished on a filter paper. This electrode was treated in 10 mM MOPS buffer (pH 7.0) containing 1% glutaraldehyde at room temperature for 30 minutes followed by 10 mM MOPS buffer (pH 7.0) containing 20 mM lysine at room temperature for 20 minutes to block glutaraldehyde. The electrode was equilibrated in 10 mM MOPS buffer (pH 7.0) at room temperature for 1 hour or longer and then stored at 4° C.

Figure 6:
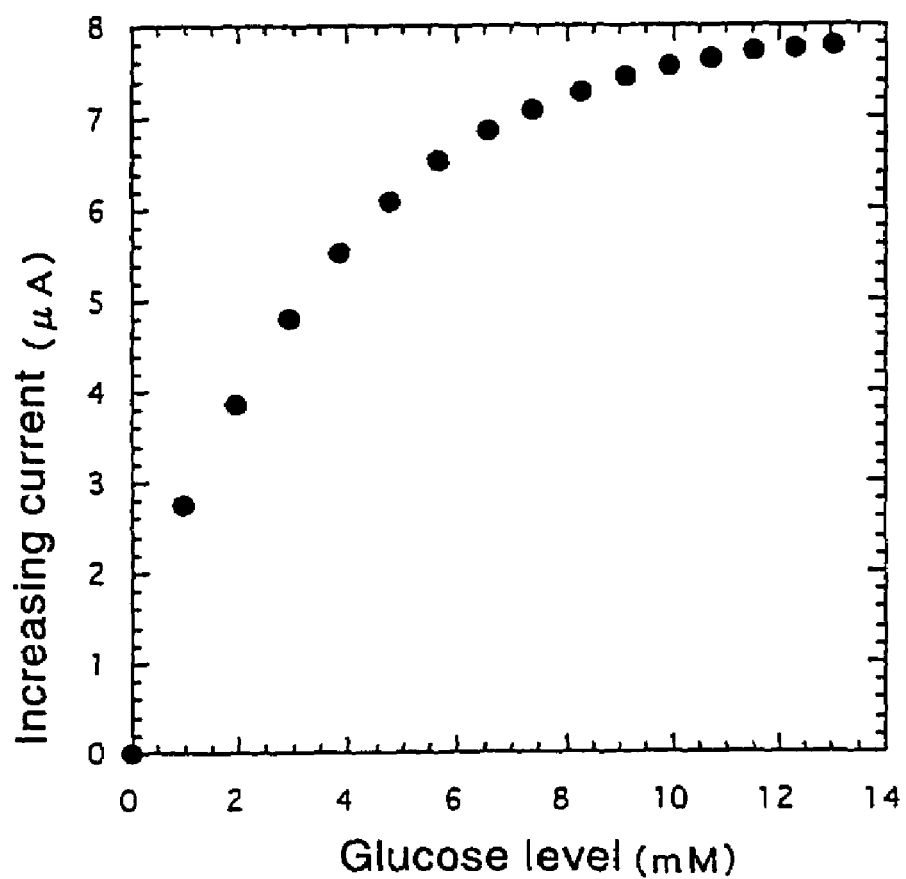
FIG. 6 shows a calibration curve of an enzyme sensor using a modified PQQGDH of the present invention.
Figure 7:
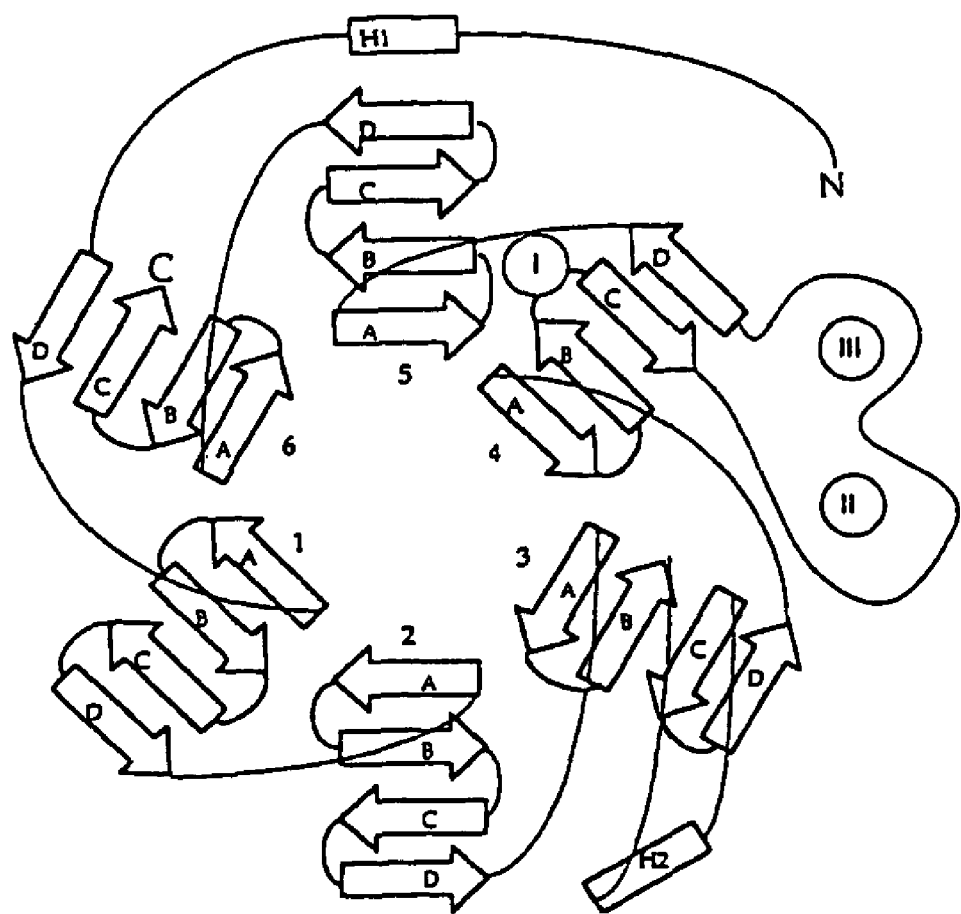
FIG. 7 shows the topology of a water-soluble GDH (Oubrie et al., FIG. 4).

Thus prepared enzyme sensor was used to measure glucose levels. FIG. 6 shows the resulting calibration curve. Thus, the enzyme sensor having a modified PQQGDH of the present invention immobilized thereon could be used for assaying glucose in the range of 1 mM–12 mM.

INDUSTRIAL APPLICABILITY

Modified PQQGDHs of the present invention have excellent thermal stability so that they are expected to provide the advantages that the enzymes can be produced at high yield with less inactivation during preparation/purification; the enzymes can be easily stored because of their high stability in solutions; the enzymes can be used to prepare an assay kit or an enzyme sensor with less inactivation; and the assay kit or enzyme sensor prepared with the enzymes has excellent storage properties because of the high thermal stability.

What is claimed is:

1. An isolated protein comprising a variant of a glucose dehydrogenase consisting of the amino acid sequence of SEQ ID NO:1, wherein said variant glucose dehydrogenase has pyrrolo-quinoline quinone as a coenzyme, wherein said variant continues to have glucose dehydrogenase activity and said variant consists of at least one amino acid substitution selected from the group consisting of:
   (1) serine at position 207 substituted with an amino acid residue selected from the group consisting of lysine, asparagine, aspartate, histidine, methionine, leucine, and cysteine;
   (2) glutamine at position 185 substituted with lysine;
   (3) glutamate at position 186 substituted with lysine;
   (4) aspartate at position 396 substituted with lysine; and
   (5) alanine at position 397 substituted with aspartate.

2. The protein of claim 1, wherein serine at position 207 is substituted with an amino acid residue selected from the group consisting of lysine, asparagine, aspartate, histidine, methionine, leucine, and cysteine.

3. The protein of claim 1, wherein glutamine at position 185 is substituted with lysine.

4. The protein of claim 1, wherein glutamate at position 186 is substituted with lysine.

5. The protein of claim 1, wherein aspartate at position 396 is substituted with lysine.

6. The protein of claim 1, wherein alanine at Position 397 is substituted with aspartate.

* * * * *